United States Patent [19]

Robertson et al.

[11] Patent Number: 4,556,460
[45] Date of Patent: Dec. 3, 1985

[54] DEHYDRATION OF ETHANOL

[75] Inventors: George H. Robertson, Berkeley; Attila E. Pavlath, Walnut Creek, both of Calif.

[73] Assignee: The United States of America as represented by the Secretary of Agriculture, Washington, D.C.

[21] Appl. No.: 385,161

[22] Filed: Jun. 4, 1982

[51] Int. Cl.$^4$ .................. B01D 3/02; B01D 53/04; C07C 29/80
[52] U.S. Cl. .................. 203/19; 203/18; 203/41; 203/49; 203/81; 203/98; 203/DIG. 11; 203/DIG. 13; 435/161
[58] Field of Search .................. 203/18, 19, 41, 49, 203/81, 90, DIG. 13, DIG. 11, DIG. 16, 98, 94; 568/916; 435/161-165; 426/494; 44/56

[56] References Cited

U.S. PATENT DOCUMENTS

| | | | |
|---|---|---|---|
| 1,493,756 | 5/1924 | LaBour | 203/90 |
| 1,833,717 | 11/1931 | Laird | 203/49 |
| 3,411,430 | 11/1968 | Rockwell | 99/238 |
| 4,071,398 | 6/1978 | Baierl | 203/DIG. 11 |
| 4,273,621 | 6/1981 | Fornoff | 203/41 |
| 4,327,184 | 4/1982 | Johnson et al. | 203/DIG. 13 |
| 4,345,973 | 8/1982 | Ladisch et al. | 203/41 |
| 4,407,662 | 10/1983 | Ginder | 203/41 |

OTHER PUBLICATIONS

L. W. Carley: *How to Make Your Own Alcohol Fuels;* Aug. 1980, pp. 73-83.
"New Ethanol Route Wears a Low-Energy Label," *Chemical Engineering,* vol. 87, p. 103 (1980).
G. Parkinson, "Batelle Maps Ways to Pare Ethanol Costs," *Chemical Engineering,* vol. 88 (11) pp. 29,31 (1981).
R. Katzen, "Low Energy Distillation Systems," *Proceedings, Bio-Energy '80,* World Congress and Exposition, Apr. 21-24, (1980), The Georgia World Congress Center, Atlanta, Ga., pp. 422-423.
J. H. Rodriquez-Arias et al., "Heat of Vaporization for Shelled Corn", *Cereal Chemistry,* vol. 40(6), pp. 676-683 (1963).
D. S. Chung et al., "Adsorption and Desorption of Water Vapor by Cereal Grains and Their Products, Part I," *Transactions of the American Society of Agricultural Engineers,* vol. 10, pp. 549-555 (1967).

*Primary Examiner*—Wilbur Bascomb
*Attorney, Agent, or Firm*—M. Howard Silverstein; David G. McConnell; Margaret A. Connor

[57] ABSTRACT

A process and apparatus for dewatering an ethanol-water solution is disclosed wherein a carrier gas is used to vaporize the solution and transport the vapors to a sorbent where water is sorbed in preference to ethanol. The invention is particularly suited for small-scale production of fuel-grade ethanol for blending with gasoline.

16 Claims, 4 Drawing Figures

DEHYDRATION OF ETHANOL

BACKGROUND OF THE INVENTION

1. Field of the Invention

This invention relates to and has among its objects the provision of a novel method and apparatus for dewatering an alcohol-water solution. Parts and percentages are by weight unless otherwise specified.

2. Description of the Prior Art

The production of gasohol by the blending of fuel grade ethanol with gasoline has the potential for helping meet energy needs. Alcohol blends with gasoline require 99.35 percent alcohol to minimize water separation problems during distribution, storage and use. To make effective use of ethanol as a substitute fuel the energy consumed to make the fuel grade alcohol must be less than the energy obtained from ethanol (84,090 Btu/gal or 7120 cal/g).

The conventional method to concentrate an aqueous solution of ethanol involves two steps: first, a dilute ethanol-water mixture (6–12 percent ethanol) is distilled to about 95 percent; next, the solution of step one is azeotropically distilled to anhydrous alcohol having a concentration of about 99.8 percent. Distillation to concentrations above 85 percent are energy intensive because the vapor and liquid phases are very similar in composition. Full separation of vapor and liquid phases having similar composition requires both a large reflux with attendant large energy load in the rectification section of the distillation column and a large number of equilibrium contacting stages resulting in a device which is physically tall and costly. Furthermore, simple (non-azeotropic) distillation is limited with regard to ethanol-enrichment because the alcohol-water mixture forms a constant boiling azeotrope at 95.6 percent ethanol.

The theoretical amount of energy expended to distill ethanol from 5 to 100 percent calculated by balancing heat input into the system and heat lost is about 3420 cal/g. In industrial practice, the actual energy expended during distillation is lower than theoretical due to the inclusion of various heat recovery systems. The reported loss of the fuel value to distill from 10 percent to 95 percent ethanol in industrial practice is about 13–21 percent; the loss of fuel value to concentrate from 95 to 100 percent by azeotropic distillation with benzene is an additional 7–11 percent. Overall expenditure is about 1400–2400 cal/g. The capital cost to produce 100 percent ethanol with an expenditure of only about 1400 cal/g is nearly double that of a distillation plant producing 95 percent ethanol due to the inclusion of azeotropic distillation equipment and advanced design heat recovery systems.

Several alternate approaches to obtain anhydrous ethanol which eliminate the energy costly azeotropic distillation have been suggested. These include dehydrating ethanol with such materials as gypsum, calcium chloride and lime, molecular sieves, biomass materials or the like, or solvent extraction. One technique involves the use of sorbents to selectively adsorb water from an ethanol-water mix. In the Purdue process (*Chemical Engineering*, Vol. 87, p. 103, Nov. 17, 1980), ethanol-rich vapors (80–92 percent ethanol) leaving a first stage distillation at a temperature of about 78°–80° C. are passed directly onto a column of cornmeal to adsorb water and obtain anhydrous ethanol. After the column is saturated, the cornmeal is regenerated by passing hot (90°–120° C.) air over it; simultaneously, a second previously regenerated column is brought into operation. Overall energy expenditure for the distillation and sorption processes including the distillation step is about 1000 cal/g.

Disadvantages of this method are that regeneration of the cornmeal sorbent is required, ethanol adsorbed onto the cornmeal is not recovered, the sorption process must be physically connected to the distillation operation, and fusel oils (amyl acetate) generated during the distillation process pass onto the column and may lead to reduced efficiency. Furthermore, since the capacity of cornmeal to adsorb water decreases as the temperature is increased from ambient, efficiency of the sorbent is less at the temperature of the process than if the operation was carried out at lower temperatures.

SUMMARY OF THE INVENTION

The invention described herein provides a means for dewatering aqueous ethanol while obviating the above problems. In the method of the invention an ethanol-water solution is contacted with a carrier gas in a manner such that a portion of the solution is vaporized and the carrier gas becomes at least partially saturated with water and alcohol vapors. The so-saturated carrier gas is passed in the proximity of a sorbent which sorbs water vapor in preference to ethanol vapor so that the carrier gas subsequent to passing over the sorbent contains a ratio of ethanol to water which is greater than that prior to passing over the sorbent. The concentrated ethanol is collected. The circulation of the carrier gas during the contacting and passing steps is carried out without contact with the outside atmosphere.

The apparatus of the invention comprises a reservoir for containing an ethanol-water solution, means for feeding a carrier gas into the reservoir to contact and vaporize a portion of the ethanol-water solution and at least partially saturate the carrier gas with ethanol-water vapors, a container for holding a sorbent which sorbs water vapor in preference to ethanol vapor, piping means connecting said reservoir and said container to circulate the carrier gas to and from the reservoir and container and to prevent contact of the carrier gas with the outside atmosphere during the vaporization and sorption steps, and a pump for pumping the carrier gas to and from the reservoir and container.

The primary advantage of the invention over the azeotropic distillation method is the great reduction in energy expended. The energy of the invention consumes about 100 cal/g to produce 99.35 perent ethanol from 95 percent ethanol versus 498–783 cal/g for the industrial azeotropic process. In addition, capital outlay and maintenance costs for the sophisticated equipment required for azeotropic distillation are eliminated.

The instant invention is distinguishable from the prior art sorbent (Purdue) process in that the latter is physically connected to the distillation column and dewaters hot ethanol vapors leaving the column, that is, the ethanol-water mix is vaporized by the application of heat prior to contact with the sorbent. In the instant invention. vaporization of the ethanol-water solution is carried out by contacting the solution with a gas so as to vaporize a portion of the solution. Thus, while the invention may be practiced at any temperature, surprisingly it may be carried out at temperatures below the boiling point of the solution, including ambient, without the application of heat to vaporize the ethanol-water solution. Furthermore, the thermal effects of invention are self-compensating. During operation, the ethanol-water mixture is cooled as the liquid phase of the mix vaporizes and the sorbent is heated as the vapor condenses. However, since the circulating gas convects the energy from the sorbent to the liquid the temperatures tend to return to the original temperature.

The instant invention further differs from the prior art sorbent process in that the carrier gas is recirculated to and from the vaporization and sorption steps without contact with the outside atmosphere. In this way, contamination of the ethanol and sorbent by atmospheric moisture as well as loss of ethanol to the atmosphere are avoided.

Another advantage of the invention over the Purdue process is that hot vapors from a distillation column are not passed directly onto the sorbent. This prevents contamination of the sorbent by "off-spec" ethanol, that is, ethanol which is not enriched to the desired concentration such as may be produced during start-up, shutdown or uncontrolled operation of a distillation process. In addition, a process separate from the distillation step has the advantages of operation with minimum control and attention. Subsequent to start-up of the invention, the process may be operated unattended for long periods of time. Additionally, shutdown time may be preset based on the time to dewater the ethanol solution as determined by prior runs or the apparatus may be fitted with a shut-down valve which is automated by the concentration of ethanol in the saturator. This is particularly advantageous for small-scale use of the invention where labor demands must be kept to a minimum. Because of the ease of operation and simplicity of equipment and low capital outlay, the invention provides a means for small scale "home" production of fuel-grade ethanol, for example, on small farms or cooperatives.

DETAILED DESCRIPTION OF THE INVENTION

The invention may be practiced using a batch process or several batch processes to dewater ethanol. Alternately, the invention may be operated wherein the ethanol-water solution is continuously fed into the system.

Figure 1:
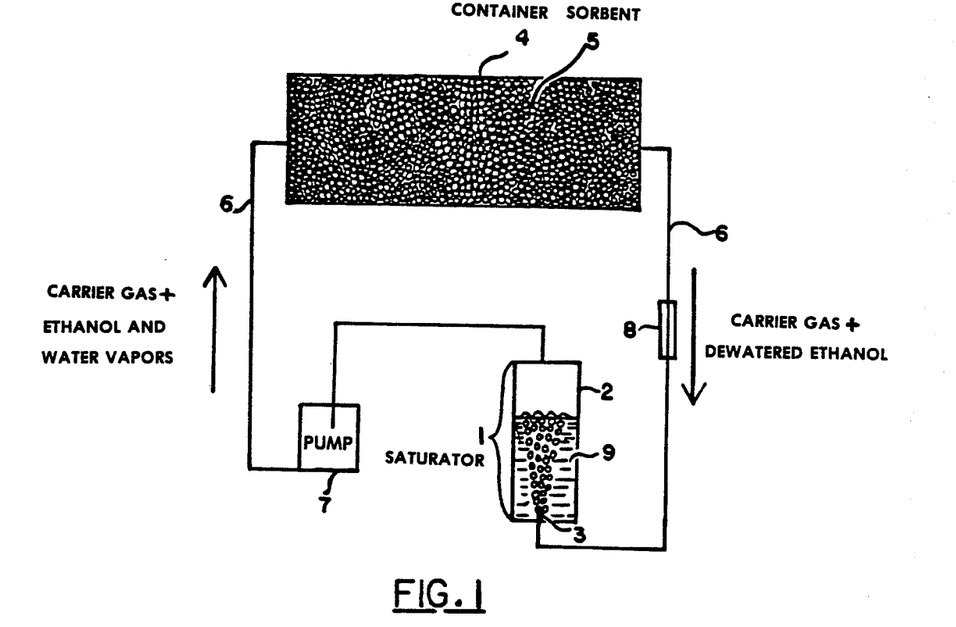
FIG. 1 is a schematic view of the batch process embodiment of the invention.

These embodiments are next described with reference to the drawings. FIG. 1 shows a batch process embodiment of the invention. Saturator 1 comprises reservoir 2 and gas sparging tube 3. Initially, reservoir 2 contains the ethanol-water solution to be dewatered. It also serves as a collection reservoir for ethanol concentrated by the method of the invention. Container 4 holds sorbent 5 which sorbs (adsorbs and/or absorbs) water vapor in preference to ethanol vapor. Piping means 6 connects saturator 1 and container 4 and provides means for circulation of the carrier gas throughout the system and prevents contact of the gas with the outside atmosphere during circulation. Pump 7 attached to pipe 6 circulates the carrier gas through the system in the direction of the arrow. Flow meter 8 monitors the flow rate of the gas.

In the method of the invention, sorbent 5, a material which sorbs water in preference to ethanol is placed in container 4. Next, ethanol-water solution 9 is placed in reservoir 2. The system is closed to the outside atmosphere and the air in the system (carrier gas) is pumped through sparging tube 3 into solution 9 causing a portion of the solution to be vaporized and causing the carrier gas to become at least partially saturated with the vapors. Next, the carrier gas containing water and ethanol vapors is circulated to sorbent 5 where water vapor is sorbed in preference to ethanol vapor. The carrier gas exiting container 4, now containing a lower water to ethanol ratio than the gas which entered the container, is circulated back to the saturator where concentrated ethanol is collected. The circulating carrier gas continues to contact the ethanol-water solution so as to vaporize a portion of the solution and become partially saturated with water and ethanol vapors and carry the vapors to sorbent 5 for preferential sorption of water. The carrier gas (and ethanol and water vapors) are circulated from the saturator and sorbent and back until the ethanol in the reservoir has been dewatered to the desired concentration.

The system is closed to the outside atmosphere during the stages where the ethanol-water solution is contacted with the carrier gas and where the gas is passed in the proximity of the sorbent. In this way contamination of the ethanol solution and sorbent by atmospheric moisture and loss of ethanol to the atmosphere is avoided during these process stages. The system is opened to remove the concentrated ethanol. Where the capacity of the sorbent is not sufficient to sorb the water in solution 9 so as to concentrate the ethanol the desired amount, the system may be opened to replace sorbent 5 with fresh sorbent. It is preferred, however, that sorbent 5 have sufficient capacity to dewater solution 9 without replacement with new sorbent.

Sparging tube 3 is a device for introducing the carrier gas into solution 9 so that at least a portion of the solution is vaporized. Such a device may include a nozzle, a pipe having perforations and the like which causes the introduced gas to vaporize some of the liquid. The carrier gas is at least partially saturated by the vaporized ethanol and water and carries the vapors to the sorbent where the water vapor is preferentially sorbed. It is not necessary that the carrier gas be in equilibrium (saturated) with the water and ethanol vapors for the invention to work. However, at least a portion of the vapors must be contained by the gas (partial saturation). The closer the carrier gas is to complete saturation, the more water vapors are transported to the sorbent and the more efficient the operation.

A critical feature of the invention is that the sorbent selected be one which sorbs (adsorbs or absorbs or both) water vapor in preference to alcohol vapor. One method for determining the selectivity of a sorbent for water over ethanol is by determining sorption isotherms. However, if equilibrium is not rapidly reached due to poor transfer of water or ethanol to or within the sorbent structure then sorption selectivity can be determined experimentally. Materials known to have the ability to sorb water in preference to alcohol are wood, plants or grains containing starch, xylan, cellulose, polysaccharides and the like.

It is preferred that the sorbent be one which can serve as feedstock for the fermentation of alcohol. In this way the energy value of the ethanol retained on the spent sorbent is not lost and energy and equipment needed to regenerate the sorbent and recover the sorbed alcohol is avoided.

Table 1 shows the losses of energy (fuel value of ethanol) which result when ethanol sorbed onto grain is not recovered. As shown, even a small loss of ethanol (1 part per 40 parts water) increases the effective energy cost by 25 percent and a somewhat larger loss (1 part per 10 parts water) causes a doubling of the energy cost for water removal.

TABLE 1

| Mass ratio of ethanol to water on sorbent (grain) | Apparent energy kcal kg of $H_2O$ removed | Effective* Energy kcal kg of $H_2O$ removed |
| --- | --- | --- |
| 0.0 | 729 | 729 |
| 0.025 | 738 | 916 |
| 0.050 | 747 | 1103 |
| 0.10 | 765 | 1477 |
| 0.20 | 801 | 2225 |
| 0.30 | 837 | 2973 |
| 0.40 | 873 | 3721 |
| 0.50 | 909 | 4470 |
| 0.60 | 945 | 5218 |
| 0.70 | 981 | 5966 |
| 0.80 | 1017 | 6715 |

*accounts for loss of fuel value.

Plants and grains and their byproducts which ferment to alcohol and are suitable as the sorbent in the practice of the invention include corn, milo, rice, wheat, sorghum and byproducts of these grains such as cornstarch and the like; wood byproducts such as wood chips, paper, and cellulose; and agricultural wastes such as cottonseed hulls, peanut shells, and rice hulls. Other materials will be obvious to those skilled in the art. If necessary, lignin-containing solids which inhibit fermentation may be removed prior to use in the method of the invention.

The maximum initial moisture content of the sorbent required to dewater the ethanol solution is critical. However, this value will vary depending on the percent water in the initial ethanol-water mix; the quantity, moisture content and capacity of the sorbent; and the desired final concentration of ethanol. The drier the sorbent, the more water will be sorbed from the ethanol solution. If it is desired that the product obtained by the invention be very dry, that is above 99% alcohol, then the sorbent must be very dry. The amount of water which a sorbent can contain and still serve as a desiccant for water can be determined from a moisture sorption - null response curve which determines the sorption properties of the sorbent under dynamic conditions. An ethanol-water solution of a known moisture content is vaporized with a carrier gas as described previously and passed over a sorbent having a known moisture content for a fixed period of time. This is repeated for a range of ethanol-water solutions and range of sorbent moisture contents. The conditions where the ethanol solution is not dewatered by the sorbent is the null point. To be a desiccant for water, the sorbent must be drier or the ethanol solution more dilute than at the null point. Where it is desired that the sorbent dewater the alcohol in the saturator to a certain level without changing of the sorbent during the process, the water sorbing capacity of the sorbent must be greater than or equal to the amount of water to be sorbed.

Means for initial drying of the sorbent include conventional means such as sun drying, hot-air expansion, oven drying, explosive puffing (gun puffing), the passing of hot air over the sorbent, or vacuum drying. A preferred method of drying of the sorbent is hot-air expansion (popping) because this process physically alters the sorbent so as to improve sorption properties. It is theorized that this method of rapid thermal expansion increases the efficiency of the sorbent by exposing more sorbent sites to the ethanol-water vapors, increasing the total residence time of the vapors in the vicinity of the sorbent and reducing the distance in the sorbent particle along which the water must diffuse to reach a sorbent site. Grains such as corn, milo and the like may be heat expanded by conventional means or by the apparatus described in U.S. Pat. No. 3,411,430 (Rockwell). Wood chips and other cellulosic substrates may be heat expanded by heating in a closed chamber followed by rapid release of pressure. Grains may also be expanded by this method. A further advantage of heat expansion (popping) of the sorbent followed by exposure to ethanol vapor is that the sorbent is sterilized which is a necessary preprocessing step for feedstock for fermentation.

Since the sorption of water and ethanol vapors onto the sorbent appears to be a rate controlled phenomenon at ambient temperature, particle size and nature of the sorbent affect the rate of transfer to and into the particle. It is preferred that the particle size of the sorbent be no greater than about one twelfth the diameter of the container holding the sorbent. This is so that the sorbent will pack together and channeling of the vapors through the sorbent is avoided. Where the sorbent is to serve as a feedstock for fermentation, the particle size should be no greater than about 0.7 cm in diameter and preferably no greater than about 0.1 cm in diameter so that later grinding prior to fermentation is not required.

Air contained within the system may be used as the carrier gas. Other gases may be externally introduced by conventional means if desired. Gas flow is monitored by flow meter 8. The rate should be such that the residence time of the vapors in the proximity of the sorbent is sufficiently long so that at least a portion of the water vapor and preferably most is transferred from the carrier gas to the sorbent. The greater the amount of water vapor sorbed by the sorbent from the ethanol-water mix, the greater the efficiency of the invention, thus it is desirable to select the gas flow rate and sorbent capacity so as to maximize water sorption.

The concentration of ethanol in the reservoir may be measured by conventional means such as a hydrometer placed in the reservoir or by gas chromatography of liquid samples. Where the reservoir is fabricated of a non-transparent material, a sight window for viewing the hydrometer may be built into the reservoir.

While the invention may be practiced at any temperature, surprisingly, the ethanol-water solution can be dewatered at ambient temperature, that is, without the application of heat to vaporize the solution prior to the passing of the vapors through the sorbent. This is because the carrier gas causes the ethanol and water in solution to vaporize and circulate with the gas to the sorbent. Operation at ambient temperature has the advantage of minimizing the energy input into the system and eliminating the need for temperature control, thereby reducing energy and labor requirements. Furthermore, since the water-holding capacity of polysaccharide-containing sorbents increases as the temperature is lowered below 100° C., the capacity of the sorbent is greater during operation at ambient temperature.

A single batch process may be used to dewater ethanol or several batch systems may be operated in a manner to dewater the ethanol solution in stages. In the latter case, the sorbent in a first system is used to dewater an ethanol-water solution of a particular water content; subsequently the sorbent now containing water and ethanol vapors sorbed from the ethanol-water mix in the first stage is transferred to a second system to dewater an aqueous ethanol solution having an initial content of water greater than that of the initial solution in the first system. The sorbent is next transferred to dewater an aqueous ethanol solution in another closed system. This may be continued as desired or until the capacity of the sorbent is reached. In the multi-stage operation, the ethanol-water solutions may also be passed through several closed systems. These solutions are transferred counter to the transfer of the sorbent. Thus, ethanol is dewatered by a sorbent of a particular moisture content, and is then transferred to a system having a sorbent with a water content less than the initial water content of the sorbent in the first system. This is continued until the ethanol solution has been dewatered the desired amount within the capacity of the sorbent.

Figure 2:
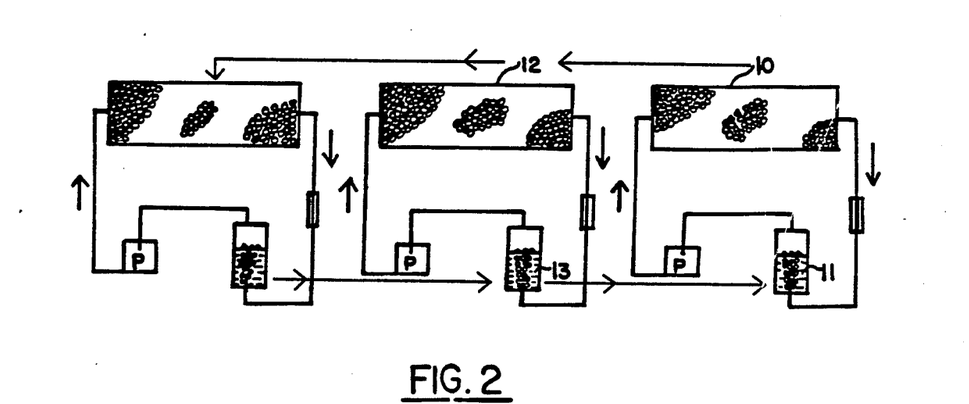
FIG. 2 depicts a multi-batch process embodiment view of the invention.

FIG. 2 schematically depicts countercurrent operation of the invention in which multiple batch systems are used to dewater ethanol. In this process, sorbent 10 having a particular moisture content is first used to dewater ethanol-water mix 11 having a particular water content. Upon completion of the dewatering process, sorbent 10—now having sorbed water vapors—is transferred to a second system as sorbent 12 to dewater ethanol solution 13 having an initial content of water greater than the water content of the initial ethanol solution (11) in the first system. This transfer of sorbent from one system successively to one containing a more dilute solution of ethanol is continued as desired to dewater ethanol or until the capacity of the sorbent is used up. For example, the sorbent may be first used to concentrate 95 percent ethanol to 99.3 percent, second to concentrate 90 percent ethanol to 95 percent, third to concentrate 85 to 90 percent and so forth.

The ethanol solutions in the saturators may be transferred countercurrent to the transfer of sorbent. In this case, an ethanol solution containing a particular percentage of water is successively transferred to a saturator where the sorbent has a moisture content sufficiently low to dewater the ethanol further. This transfer of ethanol to sorbents having successively lower moisture content is continued until the desired concentration of ethanol is reached. Where ethanol is dewatered for gasohol use, it is removed from the system at 99.35 percent ethanol.

The capacity of grain to sorb water is greater for ethanol solutions having a high percentage of water than for less dilute solutions, thus the multi-stage process maximizes the sorbing capacity of the sorbent, as shown in the table 2 below, wherein the grain is popped and milled flint corn.

TABLE 2

| Solution Wt % Change | Ratio of Absorbed Mass to Dry Grain Mass | Percent Absorbed Mass Which is Water | Mole Ratio of Water to Ethanol on Sorbent |
|---|---|---|---|
| 95–99.6 | 0.024 | 35 | 1.4 |
| 90–98.4 | 0.053 | 52 | 2.8 |
| 85–96.5 | 0.073 | 57 | 3.4 |
| 70–80 | 0.139 | 50 | 2.6 |

As shown in the Table 2, the capacity of expanded corn to sorb water is about 2½ times greater when dewatering 85 percent ethanol to 96.5 percent than when dewatering 95 to 99.6 percent. Thus if the spent sorbent from the latter is used for subsequent dewatering of a more dilute solution, the sorbent is more fully utilized.

Figure 3:
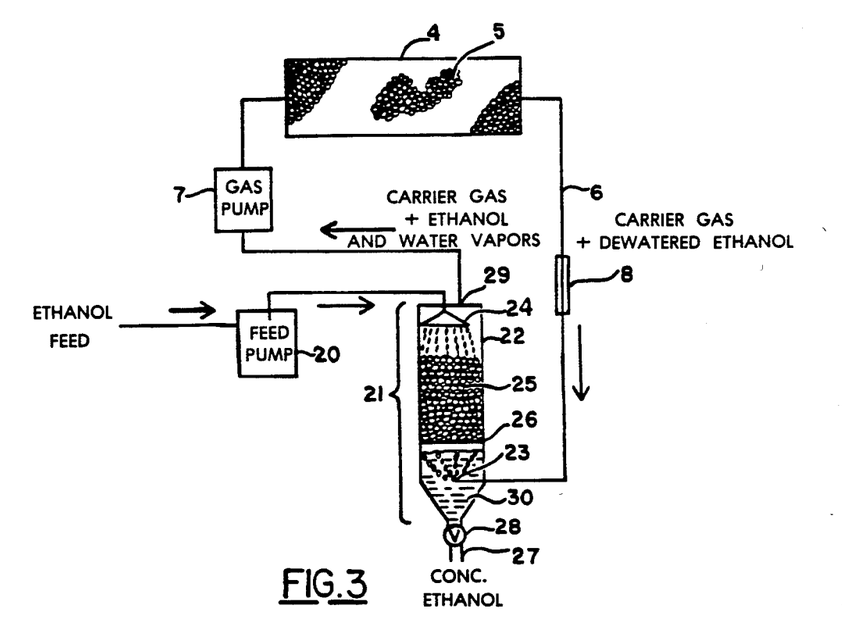
FIG. 3 depicts an embodiment wherein the feed of the ethanol water solution is continuous.

FIG. 3 depicts an embodiment of the invention wherein the ethanol-water mixture is continuously fed into the saturator and concentrated ethanol removed. Ethanol-water feed is pumped by pump 20 into saturator 21 which is comprised of reservoir 22 and gas feed means 23. In the preferred embodiment, the ethanol-water solution is fed into saturator 21 at or near the top of reservoir 22 so that the solution flows down the saturator countercurrent to the carrier gas which is fed into reservoir 22 at or near the bottom by means of gas feed means 23. This maximizes contact of the solution with the gas. Concentrated ethanol 30 is collected in the bottom of reservoir 22. Gas feed means 23 may be located so as to feed the carrier gas into reservoir 20 either into or above the concentrated ethanol.

In the preferred embodiment, the ethanol-water solution is fed into saturator 21 through flow dispenser 24 which breaks up the liquid into droplets so as to create a larger surface area of the liquid and distributes the droplets across the top of the reservoir. The droplets travel down the saturator and through inert packing material 25 supported on perforted plate 26. The packing material serves to maintain the large surface area of the liquid, slow down the rate of travel of the liquid and cause it to have intimate contact with the carrier gas which enters the reservoir through gas feed means 23. The carrier gas entering the saturator flows upward and contacts the ethanol-water solution and vaporizes at least a portion of the solution as the solution travels down the reservoir from the dispenser. As in the batch process, the carrier gas becomes at least partially saturated with ethanol and water vapors. The gas vapors are pumped by means of pump 7 through piping means 6 to container 4 containing sorbent 5 which sorbs water vapor in preference to ethanol vapor. The gas leaving the sorbent, which now has a lower water to ethanol ratio, is circulated to saturator 21, where concentrated ethanol 30 is collected in the bottom of reservoir 22. Concentrated ethanol is removed from the reservoir through exit tube 27 as controlled by valve 28. The flow of the carrier gas is monitored by means of flow meter 8. The carrier gas is recirculated through the ethanol-water feed to contact and vaporize it and passed in the proximity of the sorbent similar to the batch process. As with the batch process, the carrier gas is closed to the outside atmosphere during the contacting and passing stages to prevent contamination with atmospheric moisture. After the capacity of the sorbent to dry ethanol is reached, the system is opened and the spent sorbent is replaced.

It is preferred in the continuous-flow embodiment that the flow rates of the ethanol-water feed solution and the carrier gas be adjusted so that the water and ethanol vapors in the carrier gas leaving the saturator at point 29 are approximately in equilibrium with the water and ethanol in the feed solution. This maximizes the water carrying capacity of the gas vis-a-vis the water concentration in the feed liquid. Furthermore, the concentration of water in the gas circulated to the sorbent is maximized, thereby making greatest use of the sorbent since the capacity of the sorbent to sorb water is greater for solutions having higher concentrations of water as shown in Table 2. By maximizing both the water content of the gas circulated to the sorbent and the watersorbing capacity of the sorbent, the amount of carrier gas recirculated and the amount of sorbent used is minimized.

The required characteristics of the sorbent, methods of drying the sorbent, and carrier gas, as described for the batch process also apply to the continuous feed process.

Figure 4:
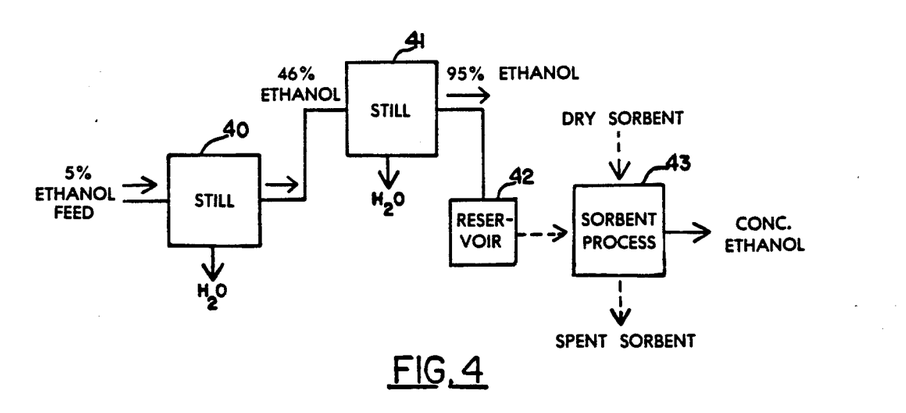
FIG. 4 depicts a system incorporating the embodiment of FIG. 3.

FIG. 4 depicts a system incorporating the continuous ethanol-water feed embodiment shown in FIG. 3 in combination with another means for dewatering ethanol such as a still. This is by way of illustration and not limitation. This system is illustrated with the limitation that the spent sorbent serve as feedstock for the fermentation of alcohol, thus the amount of grain or other material used as the sorbent is restricted to the amount to be used for fermentation. In Example A, 5 percent ethanol such as derived from grain fermentation is distilled from 5 to 46 percent and 46 to 95 percent using stills 40 and 41, respectively. The dewatered ethanol from still 41 is collected in reservoir 42 which also serves as feed source of the ethanol-water solution to sorbent process 43. Next, the ethanol-water solution is dewatered to anhydrous ethanol using the method of the invention. Spent grain is used as feed for fermentation. In Example B, ethanol is dewatered from 5 to 46 percent and 46 to 77 percent in stills 40 and 41 and from 77 to 100 percent in sorbent process 43.

The amounts of energy required to dewater 5 percent ethanol to 100 percent by the FIG. 4 embodiment are tabulated in Table 3. These calculations assume that the sorbent process is carried out at 22° C. and the sorbent contains 0% moisture before contact with the ethanol-water vapors. Heat recovery due to subsequent fermentation of the sorbent is not included. The distillation values are theoretical values calculated by heat balance. As stated previously, these values would be lower in industrial practice depending on the heat recovery system used.

TABLE 3

| PROCESS | ETHANOL DEWATERED (WEIGHT PERCENT) | | ENERGY EXPENDED (cal/g) | | |
|---|---|---|---|---|---|
| | DISTILLA-TION | SOR-BENT | DISTILLA-TION | SOR-BENT | NET |
| Fig. 4, Ex. A | 5–95 | 95–100 | 2600 | 100 | 2700 |
| Fig. 4, Ex. B | 5–77 | 77–100 | 2177 | 400 | 2577 |
| Conventional Distillation | 5–100 | | 3420 | | 3420 |

The invention is further demonstrated by the following illustrative examples:

EXAMPLE 1

Hot air expansion (popping) as a method of moisture reduction and surface expansion 400 gm samples each of milo, yellow corn and small kerneled flint corn at native moisture levels of 11.85, 13.06 and 12.21 percent (wet basis), respectively, were popped in a Midland Ross Surface Combustion Pilot Toaster at 215°–227° C. for 75 sec. Final moisture contents were 1.66, 4.75 and 2.08 percent (wet basis), respectively. Expansion volumes (ratio of expanded volume to initial volume) obtained were 3.25, 1.48 and 26.5, respectively.

EXAMPLE 2

Effect of hot air expansion (popping) and milling on the efficiency of corn sorbent Popped Corn:

A. 100 gm of small-kerneled flint corn having a moisture content of 13.91 percent was popped in a Midland Ross Surface Combustion Pilot Toaster at 216°–227° C. for 75 sec. The expansion volume obtained relative to the unpopped grain was 26.5:1; final moisture content was 2.12 percent. The popped grain was milled in a rotary-cutter mill fitted with a 2 mm screen to a particle size of about 0.7 mm diameter and further dried in hot air at 120° C. to a moisture content of 0.82 percent. The corn sorbent was packed to a depth of 40.6 cm in a 7.6 cm diameter column and the sorbent column connected to a pump and saturator as shown in FIG. 1. Thirty gm of 95.1 percent ethanol was placed in the saturator. The system was closed and the pump adjusted to an air flow of 4.49 liters per minute. Ambient temperature during operation was 21° C. The desired concentration of 99.35 percent ethanol in the saturator was reached in 152 minutes.

B. 100 gm of yellow dent corn having a moisture content of 3.06 percent was popped at 216°–227° C. for 75 sec. as described in Example A. The expansion volume obtained was 1.48:1; final moisture content was 4.99 percent. The popped corn was milled in a rotary-cutter mill fitted with a 2 mm screen to a particle size of about 0.58 diameter and further dried at 120° C. to a moisture content of 0.78 percent. The sorbent was packed to a depth of 4.2 cm in a 7.6 cm diameter column and the sorbent column connected and operated as in Example A. Starting with a 30 gm solution of 95.1 percent ethanol, a concentration of 99.1 percent ethanol was reached in the saturator in 152 minutes and 99.35 percent was reached in 244 minutes.

Unpopped Corn:

C. 100 gm of small-kerneled flint corn having a moisture content of 13.91 percent was milled in a rotary-cutter mill to a particle size of about 0.9 mm diameter and dried to a moisture content of 0.96 percent. The sorbent was packed to a depth of 3.2 cm in a 7.6 cm diameter column and connected and operated as in Example A. Starting with a 30 gm solution of 95.1 percent ethanol in the saturator, a concentration of 97.2 percent was reached after 152 minutes and 97.5 percent after 190 minutes.

D. 100 gm of yellow dent corn having a moisture content of 13.06 percent was milled in a rotary-cutter mill to a particle size of about 0.75 mm diameter and dried to a moisture content of 0.86 percent. The sorbent was packed to a depth of 3.3 cm in a 7.6 cm column and connected and operated as in Example A. Starting with a 30 gm solution of 95.1 percent ethanol in the saturator, a concentration of 99.0 percent ethanol in the saturator was reached after 152 minutes and 99.2 percent ethanol was reached after 244 minutes.

EXAMPLE 3

Effect of particle size on capacity of the sorbent

A. 100 gm of small-kerneled flint corn having a moisture content of 14 percent was hot-air popped as described in Example 1 and milled in a hammer mill fitted with sharpened, cutting hammers and a 0.64 cm diameter screen to a particle size of about 3 mm diameter. The milled corn was dried for 4 hours in vacuum at 110° C. to a final moisture content of 0 percent. The sorbent was packed to a depth of 42.6 cm in a 7.6 cm diameter column and the column was connected to a saturator as described in FIG. 1. Thirty gm of 94.9 percent ethanol was placed in the saturator; the system was closed and the air flow adjusted to 5.07 liters per minute. Ambient temperature was 22° C. A maximum concentration of 99.4 percent ethanol was reached in 150 minutes. Continued circulation of the ethanol vapors to the sorbent did not further concentrate the ethanol in the saturator indicating that the maximum capacity of the sorbent had been reached.

B. 100 gm of small-kerneled flint corn was popped, milled and dried as in Example 3A except that the mill screen was 0.16 cm diameter and particles produced were about 0.7 mm diameter. The sorbent was packed to a 42.6 cm depth in a 7.6 cm diameter column and connected and operated as in Example 3A. Starting with a 30 gm solution of 94.9 percent ethanol in the saturator, a concentration of 99.4 percent ethanol was reached after 150 minutes. Circulation of gas flow was continued and a concentration of 99.7 percent ethanol was reached after 230 minutes indicating that the smaller diameter sorbent had greater sorption capacity.

EXAMPLE 4

Dewatering of ethanol using a multi-batch process 100 gm of small-kerneled flint corn at 13.91 percent moisture was prepared by popping and milling as in Example 2A and dried in a 120° C. air to a moisture content of 0.62 percent. The sorbent was packed to a depth of 44 cm in a 7.6 cm diameter column and connected and operated as in Example 2A. 30 gm of 95.1 percent ethanol solution was concentrated to 99.3 percent in 150 minutes. At this point, the first saturator was removed and replaced with a second saturator which contained 30 gm of 90.3 percent ethanol solution. The apparatus was again connected and operated as in Example 2A. The solution in the saturator was concentrated to 96 percent in 150 minutes.

EXAMPLE 5

Determination of a moisture sorption-null response curve 100 gm of small-kerneled flint corn was hot-air popped at 216°–227° C. for 75 sec. and milled in a hammer mill fitted with sharpened, cutting hammers and a 0.635 diameter screen. Final particle size and moisture content of the corn was 3 mm and 2.4 percent, respectively. The corn was exposed to the atmosphere until a moisture content of 6 percent was reached as determined by material balance and weight gain. The sorbent was packed to a depth of 40 cm in a 7.6 cm diameter column and connected to a pump and saturator as shown in FIG. 1. Eighteen gms of 3.5 weight percent water in ethanol was placed in the saturator. A sample was drawn and the system was assembled and closed. The gas flow was adjusted to 5.07 liters per minute. Operation was continued for 2 minutes, stopped, the saturator disconnected and the saturator liquid resampled. The concentration of each sample was determined by gas chromatography and differences between the samples noted. It was found that the water content in the saturator increased by 0.1 weight percent units, thus water was transferred from the sorbent to the saturator. Next, the saturator was connected and a solution of 5 percent was substituted in the saturator. Operation was continued as described above. Water content in the saturator increased 0.05 weight percent units. This procedure was repeated at successively higher water contents until a concentration was determined by actual measurement or by interpolation between measurements to have no change in water content. This was interpreted as the null point, that is, that concentration of the ethanol-water solution and that water content of the sorbent at which no enrichment of ethanol would be expected to occur. The procedure was repeated using popped and milled grain having higher and, where appropriate, lower moisture contents. Adjustment to higher moisture content was by exposure to the atmosphere; lower moisture contents were obtained by drying in hot air or vacuum. A null response curve was determined for each grain sample. The results are shown below:

| Grain moisture (weight percent of water, wet basis) | Null point or concentration at which no water removal was observed (weight percent of water, wet basis) |
| --- | --- |
| 1.85 | 0.5 |
| 2.96 | 1.0 |
| 4.21 | 3.4 |
| 6.82 | 6.5 |
| 6.98 | 12.5 |
| 7.25 | 26.0 |
| 7.34 | 32.5 |

While the invention has been described in connection with specific embodiments thereof, it will be understood that it is capable of further modifications. The invention is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims. Such variations include dewatering other aqueous solutions such as methanol, butanol and the like or more broadly decreasing the amount of a first liquid in a second liquid by contacting the liquids with a carrier gas to vaporize them and then passing the vapors of the first and second liquids in the proximity of a sorbent which sorbs the first liquid in preference to the second.

Having thus described our invention, we claim:

1. A process for dewatering an ethanol-water mixture, comprising:
   (a) contacting an ethanol-water liquid solution with a carrier gas to vaporize a portion of the solution to form a carrier gas-treated solution, and at least partially saturate the carrier gas with the water and ethanol vapors;

(b) passing said at least partially saturated carrier gas into contact with a sorbent which sorbs water vapor in preference to ethanol vapor thereby resulting in a gas exiting from step (b) that contains a lower water to ethanol ratio than in said at least partially saturated gas; and (c) contacting said carrier gas-treated solution with said gas containing said lower water to ethanol ratio by circulating said gas exiting from step (b) back to step (a);

wherein said carrier gas and said at least partially saturated gas are circulated without contact with the outside atmosphere.

2. The process of claim 1 further comprising:
(c) repeating steps (a) and (b) until the ethanol-water solution is sufficiently dewatered.

3. The process of claim 1 wherein said contacting of step (a) and said passing of step (b) are carried out at ambient temperature.

4. The process of claim 1 wherein said sorbent is dry sorbent.

5. The process of claim 4 wherein said dry sorbent is popped sorbent.

6. The process of claim 5 wherein said sorbent is popped corn.

7. The process of claim 1 wherein the particle size of said sorbent is not greater than about one twelfth the diameter of a container holding the sorbent during the sorption of step (b).

8. The process of claim 1 wherein said sorbent is milled to not greater than about 0.7 cm in diameter prior to the sorption of step (b).

9. The process of claim 1 further comprising using the sorbent which has sorbed water vapor as a feedstock for the fermentation of alcohol.

10. The process of claim 1 wherein said contacting of step a and said passing of step b are closed to the outside atmosphere.

11. The process of claim 10 in combination with at least one more process.

12. The process of claim 11 wherein ethanol dewatered in one process is transferred to a second process to be dewatered further.

13. The process of claim 11 wherein sorbent used to dewater an ethanol-water solution in one process is transferred to a second process to dewater an aqueous ethanol solution having an initial content of water greater than that of the initial solution in the first process.

14. The process of claim 1 wherein the ethanol-water mixture to be dewatered is continuously fed into said contacting stage of step a.

15. The process of claim 14 wherein said continuous feed of the ethanol-water mixture to be dewatered is countercurrent to the contacting of said carrier gas.

16. The process of claim 15 wherein the flow rates of said continuous feed of ethanol-water mixture and said carrier gas are adjusted so that the vapors in the carrier gas after the passing of step (b) are in equilibrium with the water and ethanol in said feed solution.

* * * * *

UNITED STATES PATENT AND TRADEMARK OFFICE
CERTIFICATE OF CORRECTION

PATENT NO. : 4,556,460

DATED : December 3, 1985

INVENTOR(S) : George H. Robertson et al.

It is certified that error appears in the above—identified patent and that said Letters Patent is hereby corrected as shown below:

In col. 10, line 39, delete "3.06" and insert -- 13.06 --.

Signed and Sealed this

Twenty-first Day of April, 1987

Attest:

DONALD J. QUIGG

Attesting Officer

Commissioner of Patents and Trademarks